US00PP15880P2

(12) United States Plant Patent
Hanes

(10) Patent No.: US PP15,880 P2
(45) Date of Patent: Jul. 19, 2005

(54) ***GERANIUM* PLANT NAMED 'AMRI CONRED'**

(50) Latin Name: *Pelargonium×hortorum*
Varietal Denomination: Amri Conred

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/818,354

(22) Filed: Apr. 5, 2004

(51) Int. Cl.[7] ..... A01H 5/00
(52) U.S. Cl. ..... Plt./325
(58) Field of Search ..... Plt./325

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Geranium* plant named 'Amri Conred', characterized by its upright, outwardly spreading and rounded growth habit; freely basal branching habit; dark green-colored leaves with distinct zonation pattern; freely flowering habit with many large flower umbels per plant; and flower umbels with numerous red and light pink bi-colored single flowers.

1 Drawing Sheet

Botanical classification/cultivar designation: *Pelargonium×hortorum* cultivar Amri Conred.

BACKGROUND OF THE INVENTION

The present invention relates to a new and distinct cultivar of *Geranium* plant, botanically known as *Pelargonium× hortorum,* commercially known as a Zonal *Geranium*, and hereinafter referred to by the name 'Amri Conred'.

The new *Geranium* is a product of a planned breeding program conducted by the Inventor in Gilroy, Calif. The objective of the breeding program is to develop new Zonal *Geranium* cultivars with good basal branching, freely flowering habit and attractive flower and foliage coloration.

The new *Geranium* originated from a cross-pollination made by the Inventor in January, 2000 of a proprietary *Pelargonium×hortorum* selection identified as code number 8502-2, not patented, as the female, or seed, parent with a proprietary *Pelargonium×hortorum* selection identified as code number 8318-2, not patented, as the male, or pollen, parent. The cultivar Amri Conred was discovered and selected by the Inventor as a flowering plant within the progeny from this cross-pollination in a controlled environment in Gilroy, Calif. in June, 2000.

Asexual reproduction of the new cultivar by terminal cuttings at Gilroy, Calif. since June, 2000 has shown that the unique features of this new *Geranium* are stable and reproduced true to type in successive generations of asexual reproduction.

SUMMARY OF THE INVENTION

The following traits have been repeatedly observed and are determined to be the unique characteristics of 'Amri Conred'. These characteristics in combination distinguish 'Amri Conred' as a new and distinct *Geranium* cultivar:

1. Upright, outwardly spreading and rounded growth habit.
2. Freely basal branching habit.
3. Dark green-colored leaves with a distinct zonation pattern.

4. Freely flowering habit with many large flower umbels per plant.
5. Flower umbels with numerous red and light pink bi-colored single flowers.

In side-by-side comparisons conducted in Gilroy, Calif., plants of the new *Geranium* differed from plants of the female parent selection in the following characteristics:

1. Plants of the new *Geranium* were more vigorous than plants of the female parent selection.
2. Plants of the new *Geranium* had a more distinct leaf zonation pattern than plants of the female parent selection.
3. Plants of the new *Geranium* and the female parent selection differed in flower color as plants of the female parent selection had scarlet-colored flowers.

In side-by-side comparisons conducted in Gilroy, Calif., plants of the new *Geranium* differed from plants of the male parent selection in the following characteristics:

1. Plants of the new *Geranium* were more vigorous than plants of the male parent selection.
2. Plants of the new *Geranium* and the male parent selection differed in flower color as plants of the male parent selection had red-colored flowers.

The new *Geranium* can be compared to the cultivar, Starburst Red, disclosed in U.S. Plant Pat. No. 9,229. However, in side-by-side comparisons conducted in Gilroy, Calif., plants of the new *Geranium* differed from plants of the cultivar Starburst Red in the following characteristics:

1. Plants of the new *Geranium* had a more distinct leaf zonation pattern than plants of the cultivar Starburst Red.
2. Plants of the new *Geranium* had fuller flowers that were not as open in form than plants of the cultivar Starburst Red.
3. Plants of the new *Geranium* were more freely flowering than plants of the cultivar Starburst Red.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Amri Conred'.

The photograph at the bottom of the sheet is a close-up view of typical flowers and leaves of 'Amri Conred'. Flower and foliage colors in the photographs may differ slightly from the color values cited in the detailed botanical description which accurately describe the colors of the new *Geranium.*

DETAILED BOTANICAL DESCRIPTION

Plants of the cultivar Amri Conred have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a fiberglass-covered greenhouse during the late spring with day temperatures about 27 to 29° C., night temperatures about 16 to 18° C. and light levels about 2,000 foot-candles. Plants used for the photographs and description were about eight to twelve weeks from planting rooted cuttings. In the following description, color references are made to The Royal Horticultural Society Colour Chart, 1995 Edition, except where general terms of ordinary dictionary significance are used.

Botanical classification: *Pelargonium×hortorum* cultivar Amri Conred.

Parentage:

*Female parent.*—Proprietary *Pelargonium×hortorum* selection identified as code number 8502-2, not patented.

*Male parent.*—Proprietary *Pelargonium×hortorum* selection identified as code number 8318-2, not patented.

Propagation:

*Type cutting.*—Terminal cuttings.

*Time to initiate roots.*—About 12 to 14 days at 24° C.

*Time to develop roots.*—About four weeks at 18 to 24° C.

*Root description.*—Fibrous, fine; white in color.

*Rooting habit.*—Freely branching.

Plant description:

*General appearance.*—Upright, outwardly spreading and rounded growth habit.

*Growth and branching habit.*—Vigorous and very freely basal branching with about 14 lateral branches. Pinching, that is, removal of terminal apices, is typically not required.

*Plant height to top of foliage.*—About 24 cm.

*Plant height to top of flower umbels.*—About 34 cm.

*Plant width.*—About 45 cm.

*Lateral branches.*—Length: About 22 cm. Diameter: About 1.2 cm. Internode length: About 1.7 mm. Texture: Pubescent. Color: 145A.

*Foliage description.*—Arrangement: Alternate, simple. Length: About 7 cm. Width: About 11.5 cm. Shape: Reniform. Apex: Rounded. Base: Cordate. Margin: Crenate to slightly serrate. Venation: Palmate. Texture, upper and lower surfaces: Velvety; pubescent. Color: Developing foliage, upper surface: 147A. Developing foliage, lower surface: 147B. Fully expanded foliage, upper surface: 146A; distinct zonation pattern about 3 cm from the margin, 1.5 cm in width and 147A in color. Fully expanded foliage, lower surface: 147B. Venation, upper surface: 144B. Venation, lower surface: 147D. Petiole: Length: About 9 cm. Diameter: About 3 mm. Texture, upper and lower surfaces: Pubescent. Color, upper and lower surfaces: 144A.

Flower description:

*Flower arrangement and type.*—Single rounded flowers arranged in hemispherical umbels arising from apical leaf axils. Umbels displayed above the foliage. At full flowering, usually about 22 open and developing umbels per plant. Flowers not persistent; umbels persistent. Flowers not fragrant.

*Flowering season.*—Year-round under greenhouse conditions. In the garden, flowering is continuous from spring until fall. Plants start flowering about eight weeks after planting.

*Flower longevity.*—Flowers last about one week on the plant.

*Umbels.*—Height: About 7 cm. Diameter: About 11.5 cm. Number of flowers and flower buds per umbel: About 40. Flower diameter: About 4 cm. Flower depth (height): About 2 cm.

*Flower buds.*—Length: About 1.9 cm. Diameter: About 8 mm. Shape: Ovoid. Color: 155A with random speckles, 50A.

*Petals.*—Quantity/arrangement: About five petals per flower in a single whorl; imbricate. Length: About 2.5 cm. Width: About 2.3 cm. Shape: Obovate. Apex: Rounded. Base: Attenuate. Margin: Entire. Texture, upper and lower surfaces: Smooth. Aspect: Slightly cupped. Color: When opening, upper surface: 155D; random speckles and splotches, 70B and 63B. When opening, lower surface: 155A; random speckles and splotches, 50B and 54B. Fully opened, upper surface: 56A; random speckles and splotches, 52A and 50A; occasionally petals may be mostly 52A in color. Towards the base, 155D; venation, 52A. Fully opened, lower surface: 55C; random speckles and splotches, 52A to 52B. Towards the base, 56A; venation, 52A to 52B.

*Sepals.*—Quantity/arrangement: Five per flower in a single whorl; not imbricate on open flowers. Length: About 1.4 cm. Width: About 4 mm. Shape: Lanceolate to elliptical. Apex: Acuminate. Margin: Entire. Texture, upper and lower surfaces: Smooth, glabrous. Color, upper surface: 144A. Color, lower surface: Towards the apex, 144A; towards the base, 185A.

*Peduncle* (*umbel stem*).—Length: About 18.5 cm. Diameter: About 4.5 mm. Angle: About 30° from vertical. Strength: Strong. Texture: Pubescent. Color: 144A.

*Pedicel* (*individual flower stem*).—Length: About 3.8 cm. Diameter: About 1 mm. Angle: Erect to about 75° from vertical. Strength: Strong. Texture: Pubescent. Color: 185A to 185B.

*Reproductive organs.*—Androecium: Anther quantity: About ten per flower. Anther size: About 1 by 2 mm. Anther shape: Oval. Anther color: 50B. Pollen amount: Scarce. Pollen color: 34B. Gynoecium: Pistil quantity: One per flower. Pistil length: About 1 cm. Stigma shape: Five-parted, star-shaped. Stigma color: 46A. Style length: About 3 mm. Style color: 46A. Ovary color: 138C.

*Seed/fruit.*—Seed and fruit development has not been observed.

Disease/pest resistance: Resistance to pathogens and pests common to *Pelargonium* has not been observed.

It is claimed:

1. A new and distinct cultivar of *Geranium* plant named 'Amri Conred', as herein illustrated and described.

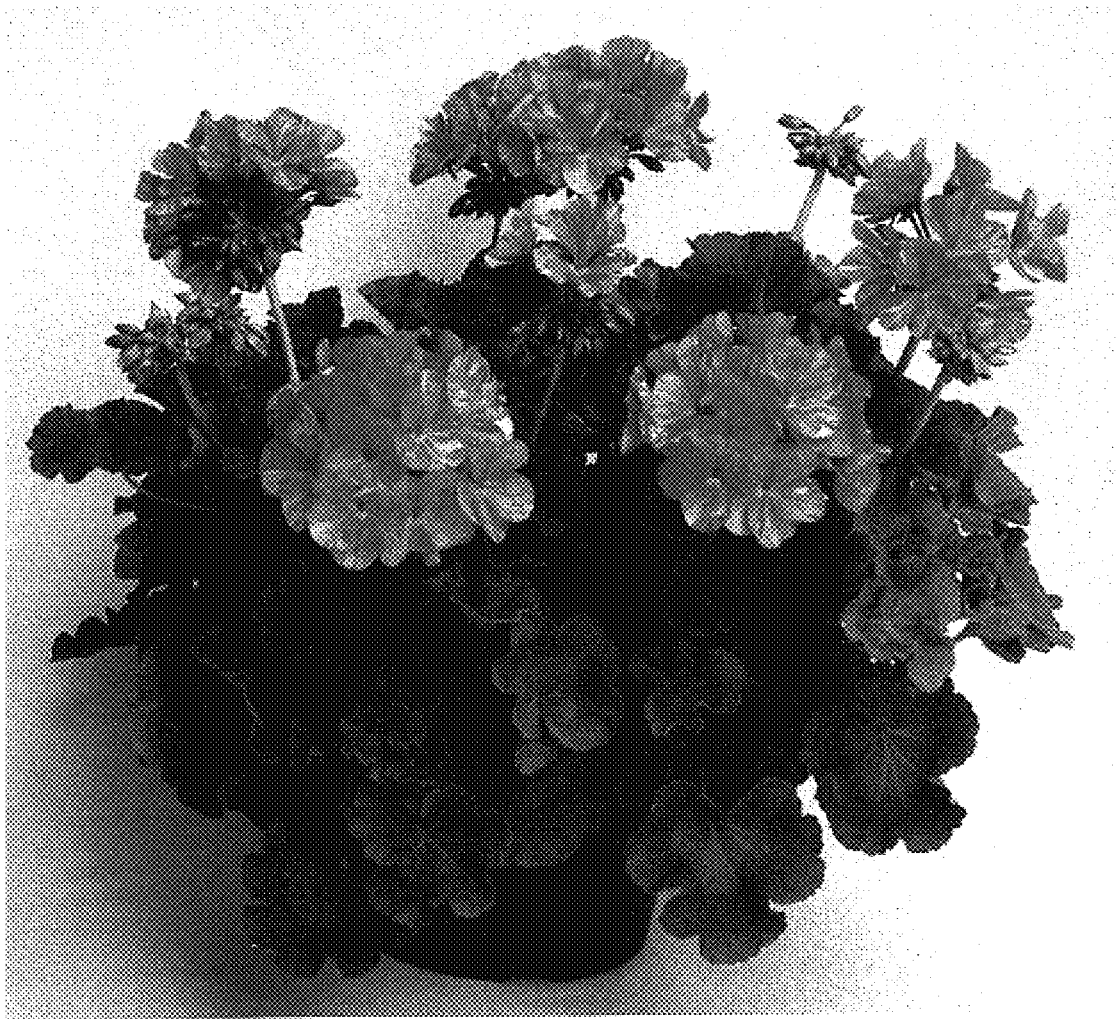
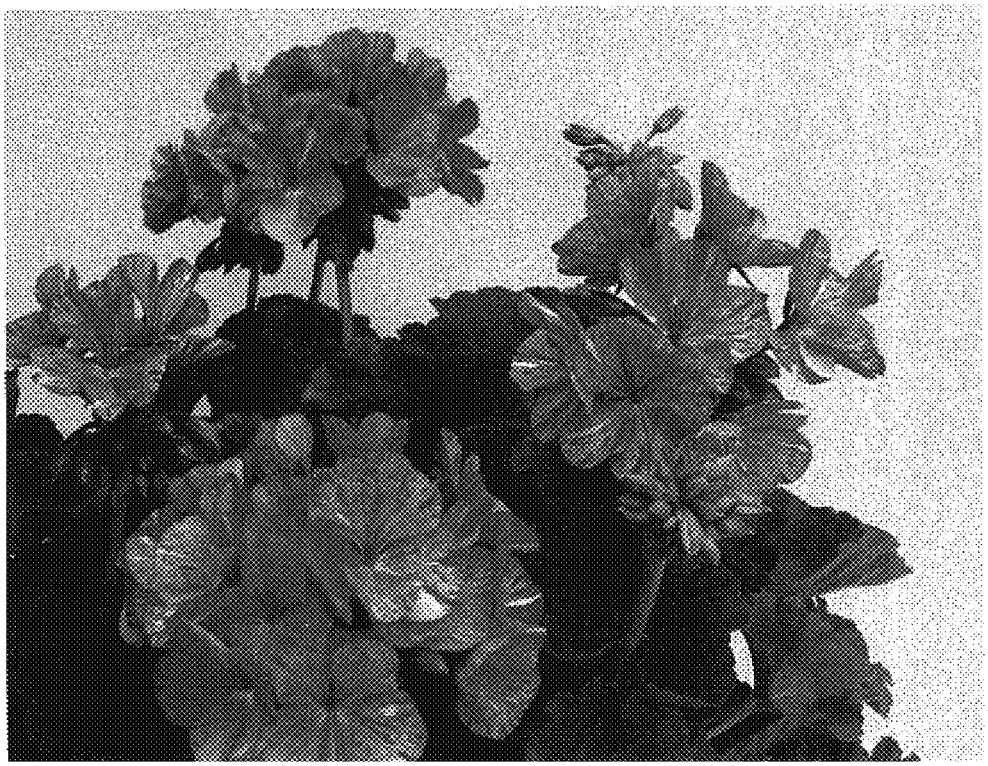

* * * * *